(12) United States Patent
Kuramori

(10) Patent No.: US 8,200,337 B2
(45) Date of Patent: Jun. 12, 2012

(54) METHOD OF SELECTING SPECIFIC SKELETAL MUSCLE HIGHLY SENSITIVE TO HUMAN PSYCHOLOGICAL STATE, DEVICE FOR SELECTING SPECIFIC SKELETAL MUSCLE, METHOD OF EVALUATING STRESS DURING WORK, AND SYSTEM FOR EVALUATING STRESS DURING WORK

(75) Inventor: Akira Kuramori, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 478 days.

(21) Appl. No.: 12/515,184

(22) PCT Filed: Nov. 13, 2007

(86) PCT No.: PCT/JP2007/072001
§ 371 (c)(1),
(2), (4) Date: May 15, 2009

(87) PCT Pub. No.: WO2008/059830
PCT Pub. Date: May 22, 2008

(65) Prior Publication Data
US 2010/0049278 A1    Feb. 25, 2010

(30) Foreign Application Priority Data

Nov. 17, 2006    (JP) .................................. 2006-311442

(51) Int. Cl.
*A61N 1/00*    (2006.01)
(52) U.S. Cl. ......................................................... 607/48
(58) Field of Classification Search .................... 434/29, 434/236; 600/383, 544, 547, 546, 300, 587; 607/2
See application file for complete search history.

(56) References Cited

U.S. PATENT DOCUMENTS

| 7,467,010 B2 | 12/2008 | Kuramori et al. |
| 2002/0111557 A1 | 8/2002 | Madill et al. |
| 2005/0245838 A1* | 11/2005 | Kuramori et al. ............ 600/546 |
| 2006/0015028 A1 | 1/2006 | Finneran et al. |
| 2007/0254270 A1* | 11/2007 | Hersh ........................... 434/236 |

FOREIGN PATENT DOCUMENTS

| JP | 2005-087486 | 4/2005 |
| WO | WO 98/22021 A1 | 5/1998 |

OTHER PUBLICATIONS

International Search Report dated Dec. 11, 2007.
European Search Report for European Application No. EP 07 83 1731 dated Mar. 1, 2010.

* cited by examiner

*Primary Examiner* — George Manuel
*Assistant Examiner* — Robert Wieland
(74) *Attorney, Agent, or Firm* — Knobbe Martens Olson & Bear LLP

(57) ABSTRACT

The selecting method and apparatus for selecting a specific skeletal muscle affected by a psychological state of a person from skeletal muscles of the person apply at least a first stimulus to the person to bring the person into an uncomfortable state, acquire muscle activity information of each of the skeletal muscles when the first stimulus is applied to the person and select the specific skeletal muscle based on the muscle activity information of each of the skeletal muscles by the first stimulus. The stress evaluating method and system acquire the muscle activity information of the person during an operation for the selected specific skeletal muscle selected by the selecting method and apparatus, and evaluate a degree of stress placed on the person during the operation based on the acquired muscle activity information.

15 Claims, 8 Drawing Sheets

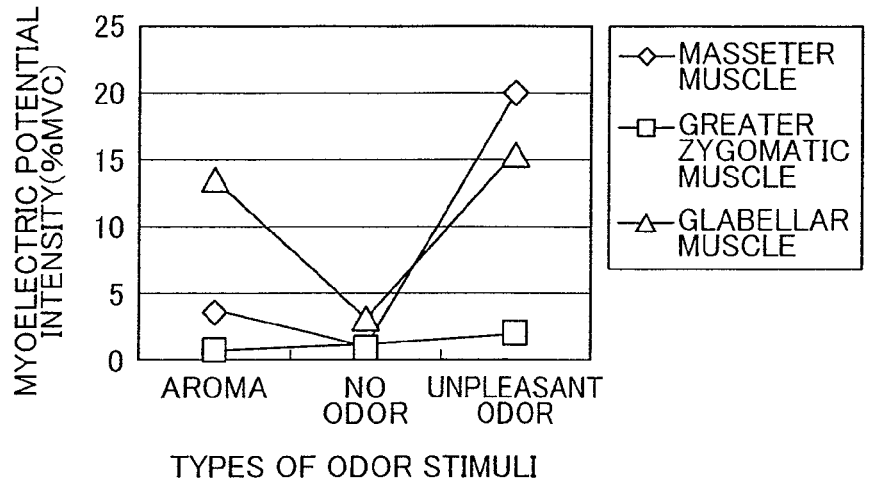
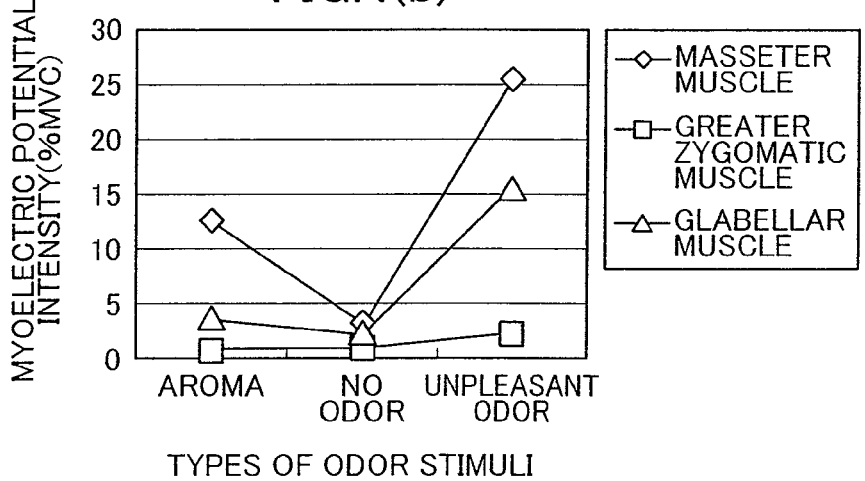
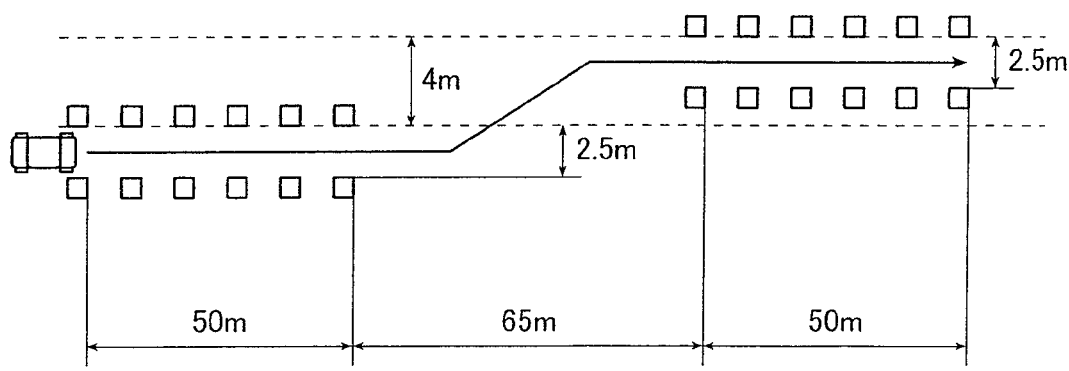

METHOD OF SELECTING SPECIFIC SKELETAL MUSCLE HIGHLY SENSITIVE TO HUMAN PSYCHOLOGICAL STATE, DEVICE FOR SELECTING SPECIFIC SKELETAL MUSCLE, METHOD OF EVALUATING STRESS DURING WORK, AND SYSTEM FOR EVALUATING STRESS DURING WORK

This application is the U.S. National Phase under 35. U.S.C. §371 of International Application PCT/JP2007/072001, filed Nov. 13, 2007, which claims priority to Japanese Patent Application No. 2006-311442, filed Nov. 17, 2006. The International Application was published under PCT Article 21(2) in a language other than English.

TECHNICAL FIELD

The present invention relates to a method and an apparatus for selecting a specific skeletal muscle highly sensitive to a psychological state of a person from a plurality of skeletal muscles of the person and a method and a system for evaluating a stress on the person during an operation.

BACKGROUND ART

In general, in a state where a psychological burden is placed on a person, specifically, in a state where the person is stressed to be tense (referred to as a stressed state), a so-called strain or stiffness corresponding to an involuntary excessive muscle activity appears. The muscle activity appearing as the strain or stiffness in the stressed state is called a stress-related muscle activity. As a technique which treats the stress-related muscle activity, for example, Patent Document 1 described below is cited. In Patent Document 1 described below, when a certain type of operation is performed, muscles which have no direct relation with the operation are selected. For the selected muscles, muscle activity information is acquired. From the stain or stiffness appearing in the muscle activities of the muscles, the degree of stress (the degree of the psychological burden) on the person is evaluated. For example, for a clenching action performed by a person during an operation (worker) when the worker feels stressed, the muscle activity information indicating the degree of the muscle activity related with the clenching is acquired. Based on the acquired muscle activity information, a state of tension of the worker is evaluated. The use of the stress-related muscle activity allows, for example, the evaluation of the state of tension with a higher time resolution as compared with the case where general stress indices (for example, those obtained by the analysis of a heartbeat interval, sweating, urine components, salivary components, blood components, and the like) are used.

Patent Document 1: JP 2005-87486 A

DISCLOSURE OF THE INVENTION

Problem to be solved by the Invention

Conventionally, as a muscle to be tested, for which the stress-related muscle activity is measured for evaluating the stress on the person, among a plurality of muscles of the person, a muscle such as a masseter muscle, in which the stress-related muscle activity is empirically considered to be likely to occur, is selected in most cases. However, the muscles which are active in the stressed state differ for each person. For example, in the stressed state, some just clench the teeth together and scarcely frown. On the other hand, others just frown and scarcely clench the teeth together in the stressed state. For the latter persons, the degree of stress on each of the persons cannot be quantitatively evaluated with good accuracy based on the muscle activity information of the masseter muscle. As described above, the stress-related muscle activity occurs in various parts of a body. However, the muscle which becomes more active in the stressed state varies for each person. Therefore, it is desired to select the muscle to be tested, which is suitable for the evaluation of the degree of stress, for each test subject. However, such a method is not proposed at present.

Therefore, the present invention has been made in view of the problem described above, and provides a method and an apparatus for selecting a muscle suitable for the evaluation of a stress during an operation based on a muscle activity for each person to enable the quantitative evaluation of a stressed state with high accuracy for each person.

Means for solving the Problem

The present invention provides a method of selecting a specific skeletal muscle affected by a psychological state of a person from a plurality of skeletal muscles of the person, comprising: a step of applying at least a first stimulus to the person to bring the person into an uncomfortable state; a step of acquiring muscle activity information of each of the plurality of skeletal muscles of the person when the first stimulus is applied to the person; and a step of selecting the specific skeletal muscle based on the muscle activity information of each of the plurality of skeletal muscles of the person when the person is brought into the uncomfortable state by the first stimulus.

Preferably, the first stimulus is a stimulus for bringing the person into the uncomfortable state.

And, it is preferable that the method of selecting the specific skeletal muscle further comprise: a step of acquiring the muscle activity information of each of the plurality of skeletal muscles of the person when the person is in a relaxing state, prior to the step of selecting the specific skeletal muscle, wherein a muscle having a larger amount of change in the muscle activity information when the person is brought into the uncomfortable state by the first stimulus with respect to the muscle activity information in the relaxing state as compared with a set first threshold value is selected as the specific skeletal muscle from the plurality of skeletal muscles of the person in the selecting step.

Preferably, a plurality of stimuli including the first stimulus for bringing the person into the uncomfortable state and a second stimulus for bringing the person into a comfortable state are sequentially applied in the step of applying the stimulus to the person; and a muscle having the larger amount of change in the muscle activity information when the person is brought into the uncomfortable state by the first stimulus with respect to the muscle activity information in the relaxing state as compared with the set first threshold value and a smaller amount of change in the muscle activity information when the person is brought into the comfortable state by the second stimulus with respect to the muscle activity information in the relaxing state as compared with a set second threshold value is selected-as the specific skeletal muscle in the selecting step.

Or, preferably, the muscle activity information of each of the plurality of skeletal muscles of the person is acquired for the each stimulus when the each stimulus is applied to the person, while subjective evaluation information of the person indicating the psychological state of the person at this time is acquired, in the step of acquiring the muscle activity information; and the psychological state of the person when the each subjective evaluation information is acquired is specified based on the subjective evaluation information of the person in the selecting step.

Here, preferably, a plurality of different stimuli are sequentially applied to the person in the step of applying the stimulus to the person; the muscle activity information of each of the plurality of skeletal muscles of the person is acquired for each of the stimuli when each of the stimuli is applied to the person, whereas the subjective evaluation information is acquired, in the step of acquiring the muscle activity information; and the psychological state of the person when the each subjective evaluation information is acquired is specified based on the subjective evaluation information of the person to specify the psychological state of the person when the each muscle activity information corresponding to the each subjective evaluation information is acquired, thereby associating the each muscle activity information with the psychological state of the person, in the selecting step.

Preferably, all the plurality of skeletal muscles of the person are muscles which are not active for an operation performed by the person.

Preferably, the plurality of skeletal muscles of the person include at least one of a masticatory muscle and a mimetic muscle of a face of the person.

In addition, the present invention provides a method of evaluating a stress on a person during an operation, comprising: a step of applying at least a first stimulus to the person to bring the person into an uncomfortable state; a step of acquiring muscle activity information of each of the plurality of skeletal muscles of the person when the first stimulus is applied to the person; a step of selecting the specific skeletal muscle based on the muscle activity information of each of the plurality of skeletal muscles of the person when the person is brought into the uncomfortable state by the first stimulus; a step of acquiring the muscle activity information of the person during the operation for the selected specific skeletal muscle of the person; and a step of evaluating a degree of stress placed on the person during the operation based on the acquired muscle activity information of the specific skeletal muscle.

Moreover, the present invention provides an apparatus for selecting a specific skeletal muscle affected by a psychological state of a person from a plurality of skeletal muscles of the person, comprising: means for acquiring muscle activity information of each of a plurality of different skeletal muscles of the person; means for applying at least a first stimulus to the person to bring the person into an uncomfortable state; and means for selecting the specific skeletal muscle based on the muscle activity information of each of the plurality of skeletal muscles of the person when the person is brought into the uncomfortable state by the first stimulus.

Preferably, the first stimulus is a stimulus for bringing the person into the uncomfortable state.

Or, it is preferable that the apparatus for selecting the specific skeletal muscle further comprise; means for acquiring subjective evaluation information of the person indicating the psychological state of the person when the muscle activity information of each of the plurality of skeletal muscles of the person is acquired, for the each stimulus when the each stimulus is applied to the person, wherein the psychological state of the person when the each subjective evaluation information is acquired is specified based on the subjective evaluation information of the person acquired by the means of acquiring the subjective evaluation information.

Preferably, the selecting means receives the muscle activity information of each of the plurality of different skeletal muscles of the person when the person is in a relaxing state to select a muscle having a larger amount of change in the muscle activity information when the person is brought into the uncomfortable state by the first stimulus with respect to the muscle activity information in the relaxing state as compared with a set first threshold value, as the specific skeletal muscle from the plurality of skeletal muscles of the person.

The present invention further provides a system for evaluating a stress during an operation, comprising: an apparatus for selecting a specific skeletal muscle affected by a psychological state of a person from a plurality of skeletal muscles of the person, the apparatus comprising: means for acquiring muscle activity information of each of a plurality of different skeletal muscles of the person; means for applying at least a first stimulus to the person to bring the person into an uncomfortable state; and means for selecting the specific skeletal muscle based on the muscle activity information of each of the plurality of skeletal muscles of the person when the person is brought into the uncomfortable state by the first stimulus; means for acquiring the muscle activity information of the specific skeletal muscle of the person during the operation, the specific skeletal muscle of the person being selected by the apparatus for selecting the specific skeletal muscle; and means for evaluating a degree of the stress placed on the person during the operation based on the acquired muscle activity information of the specific skeletal muscle.

Here, preferably, the first stimulus is a stimulus for bringing the person into the uncomfortable state.

Or, it is preferable that the system for evaluating the stress during the operation further comprise: means of acquiring subjective evaluation information of the person indicating the psychological state of the person when the muscle activity information of each of the plurality of skeletal muscles of the person is acquired, for the each stimulus when the each stimulus is applied to the person, wherein the psychological state of the person when the each subjective evaluation information is acquired is specified based on the subjective evaluation information of the person acquired by the means of acquiring the subjective evaluation information.

EFFECTS OF THE INVENTION

According to the present invention, the muscle suitable for the evaluation of the stress during the operation based on the muscle activity is selected for each person to quantitatively evaluate the stress during the operation with high accuracy for each person. As a result, the degree of stress placed on the worker during the operation can be quantitatively evaluated with relatively high accuracy. For example, the stress, to which a driver driving a vehicle is subjected, can be quantitatively evaluated with high accuracy. For example, for each of the cases where a plurality of different sets of tires are mounted to a specific vehicle, the stress, to which a specific driver is subjected when the specific driver continuously drives the specific vehicle, can be quantitatively evaluated with high accuracy. Moreover, the driver can quantitatively know with high accuracy which tire provides which degree of indefatigability. By using such information, the tire which is less stressful for the driver, specifically, the tire which hardly fatigues the driver can be efficiently developed. By using the present invention, the relation of the stress on the driver not only with the tires but also with various conditions such as the vehicle, a vehicle control system, and environments (road design, road surface, and weather) can be easily identified in a specific manner.

BRIEF DESCRIPTION OF THE DRAWINGS

[FIGS. 4] These (a) and (b) are graphs obtained by carrying out the method of evaluating the stress according to the first embodiment, illustrating degree of sensitivity of each of a plurality of skeletal muscles to a psychological state of the person.

[FIG. 5] This is a view for illustrating a driving course of a vehicle driven and manipulated by the person in the method of evaluating the stress according to the first embodiment.

Figure 1:
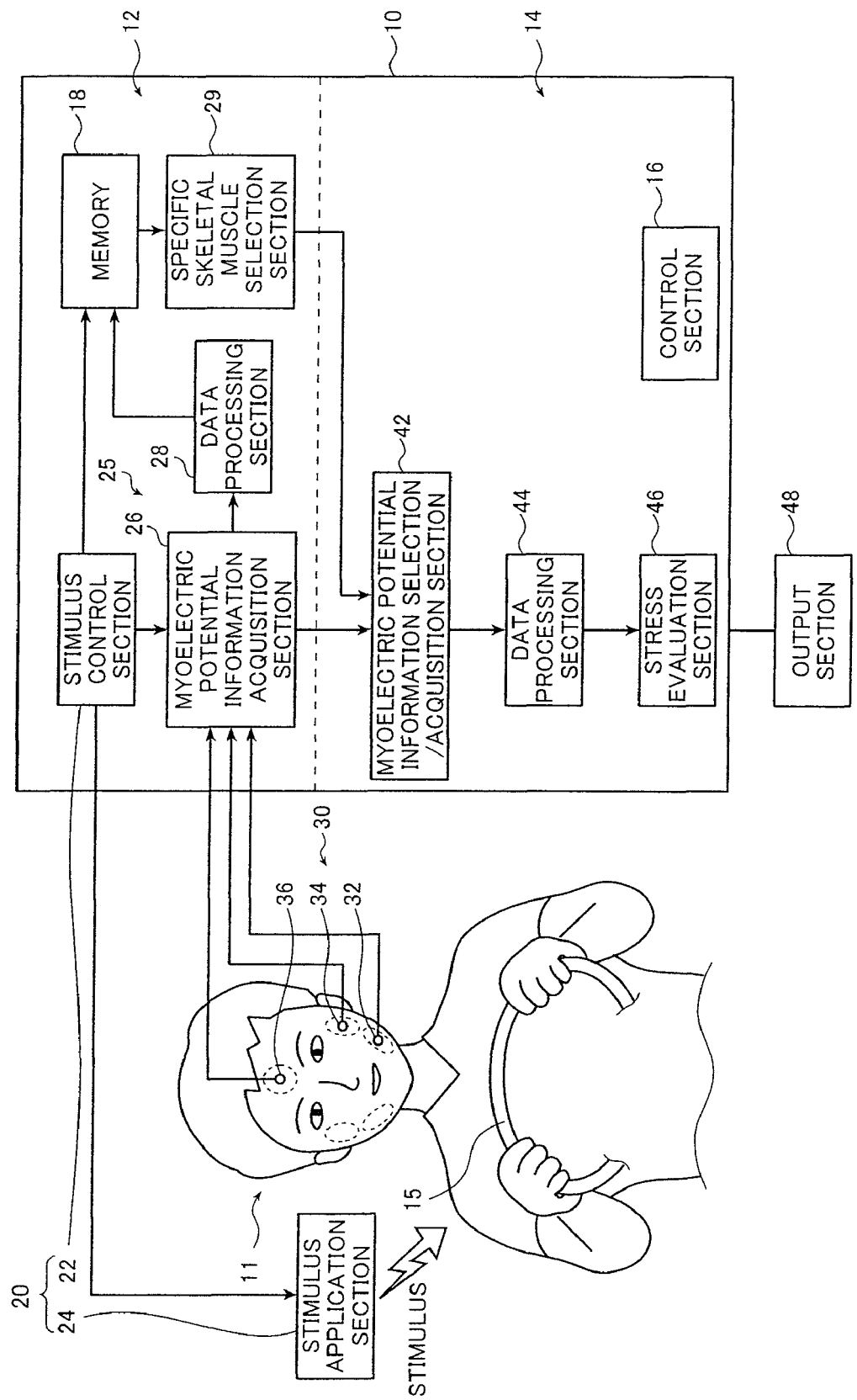
[FIG. 1] This is a schematic configuration diagram for illustrating an example of the first embodiment of a system for evaluating a stress during an operation according to the present invention.

DESCRIPTION OF THE REFERENCE NUMERALS 10 evaluation system
11 person
12 selection apparatus
14 stress evaluation apparatus
15 steering wheel
16 control section
18 memory
20 driver stimulating mechanism
22 stimulus control section
24 stimulus application section
25 muscle activity information acquisition mechanism
26 myoelectric potential information acquisition section
28 data processing section
29 specific skeletal muscle selection section
30 myoelectric potential detection sensor unit
32, 34, 36 detection sensor pair
38 earth electrode
42 myoelectric potential information selection/acquisition section
44 data processing section
46 stress evaluation section
48 output section
60 subjective information acquisition mechanism
62 input section
64 subjective information acquisition section

BEST MODE FOR CARRYING OUT THE INVENTION

Hereinafter, a method and an apparatus for selecting a specific skeletal muscle highly sensitive to a psychological state of a person, and a method and a system for evaluating a stress during an operation according to the present invention are described based on preferred embodiments illustrated in the accompanying drawings.

First, the first embodiment is described. FIG. 1 is a schematic configuration diagram for illustrating an evaluation system 10 corresponding to the first embodiment of the system for evaluating the stress during the operation according to the present invention. The evaluation system 10 is a system for evaluating a stress on a person 11 who drives a vehicle. The stress is generated with a driving manipulation of the person 11, for example, a steering operation for driving a steering wheel 15 to steer a vehicle (not shown).

The evaluation system 10 includes a selection apparatus 12 corresponding to an example of the apparatus for selecting the specific skeletal muscle according to the present invention and a stress evaluation apparatus 14 for evaluating the degree of stress placed on the person 11 during the steering operation based on myoelectric potential information of the specific skeletal muscle selected by the selection apparatus 12.

The evaluation system 10 according to this embodiment includes the selection apparatus 12 and the stress evaluation apparatus 14 in an integrated form, as illustrated in FIG. 1. Each section of each of the apparatuses functions by the control and management of a control section 16. The evaluation system 10 may be constituted by a known computer including sections, each functioning by the execution of software stored in a memory 18 by a CPU (not shown), or may also be constituted by a dedicated apparatus including the sections, each being constituted by a circuit. In this embodiment, the evaluation system 10 is provided in the vehicle (not shown) driven by the person 11. In the system for evaluating the stress during the operation according to the present invention, the apparatus for selecting the specific skeletal muscle highly sensitive to the psychological state of the person (hereinafter, referred to as a highly-sensitive skeletal muscle) and the stress evaluation apparatus for evaluating the degree of stress may be constituted as separate units. The apparatus for selecting the highly-sensitive skeletal muscle does not need to be placed in the vehicle. It is also preferred to select the specific skeletal muscle of the person 11, which is described below, at a location other than in the vehicle, for example, in an isolated room or the like.

The selection apparatus 12 selects the specific skeletal muscle highly sensitive to the psychological state of the person 11 from a plurality of the skeletal muscles of the person 11. The selection apparatus 12 includes: a driver stimulating mechanism 20 for applying a stimulus for making the person 11 uncomfortable or a stimulus for making the person 11 comfortable; a muscle activity information acquisition mechanism 25 for acquiring muscle activity information of each of the plurality of different skeletal muscles of the person 11 in each of a plurality of psychological states of the person 11 such as a relaxing state, an uncomfortable state, and a comfortable state of the person 11; and a specific skeletal muscle selection section 29 for selecting the specific skeletal muscle of the person 11 based on the muscle activity information of each of the plurality of skeletal muscles.

The driver stimulating mechanism 20 includes a stimulus control section 22 and a stimulus application section 24. The stimulus application section 24 is a section for applying the stimulus to the person 11. As the stimulus to be applied to the person 11, an algesic stimulus (pain stimulus), an olfactory stimulus (odor stimulus), an auditory stimulus (sound stimulus), and the like are exemplified. When the pain stimulus is applied to the person 11, it is sufficient that the stimulus application section 24 is, for example, a known finger-pressure device. When the odor stimulus is applied to the person 11, it is sufficient that the stimulus application section 24 is, for example, an aroma generator or the like. When the auditory stimulus is applied to the person 11, it is sufficient that the stimulus application section 24 is, for example, a sound generator. The type of stimulus (the type of aroma, the type of sound, the type of pain, or the like) applied to the person 11 by the stimulus application section 24 and the degree thereof are controlled by the stimulus control section 22. The stimulus control section 22 controls an operation of the stimulus application section 24 to allow the stimulus according to a stimulus condition stored and set in advance in, for example, the memory 18 to be applied to the person 11, thereby applying the stimulus to the person 11 according to the stimulus condition. It is sufficient that the stimulus condition as described above is input and set in advance by input means (not shown) such as a keyboard or a mouse. The stimuli applied by the stimulus application section 24 bring the person 11 into various different psychological states such as the relaxing state, the comfortable state, and the uncomfortable state. This first embodiment is suitably carried out when the psychological state of the person 11 can be clearly defined by the stimulus applied by the stimulus application section 24, for example, when the stimulus forcibly causes the psychological state of the person 11 to be the uncomfortable state. For example, the stimulus application section 24 is configured to release an aroma to bring the person 11 into the comfortable state and to release a distinct unpleasant odor to bring the person 11 into the uncomfortable state.

The muscle activity information acquisition mechanism 25 acquires muscle activity information, for example, information of a myoelectric potential intensity of each of the plurality of different skeletal muscles of the person 11 in each of the various psychological states of the person 11 such as the relaxing state, the comfortable state, and the uncomfortable state of the person 11. The muscle activity information acquisition mechanism 25 includes a myoelectric potential detection sensor unit 30, a myoelectric potential information acquisition section 26, and a data processing section 28.

Figure 2:
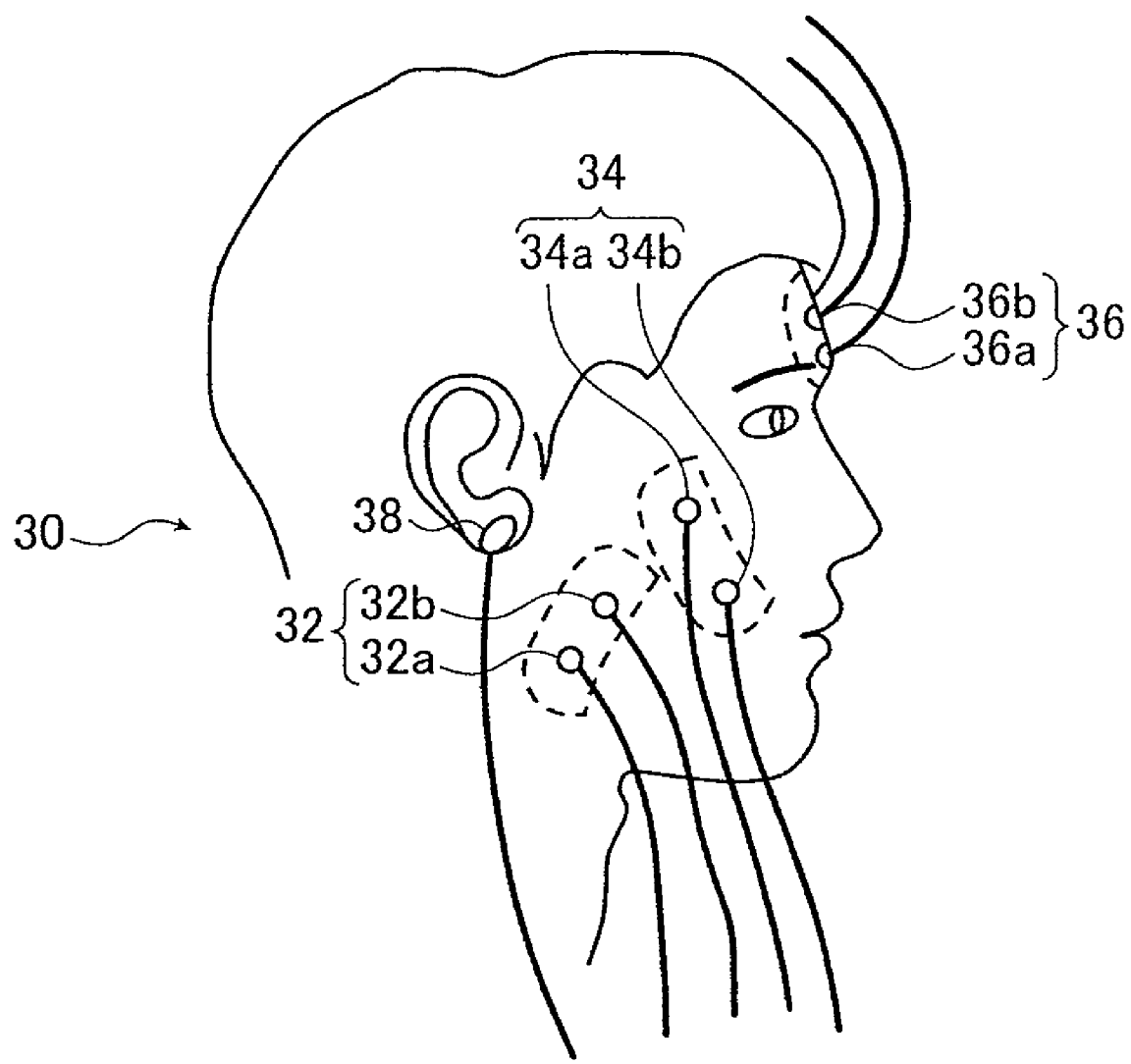
[FIG. 2] This is a schematic side view for illustrating an attachment position for attaching a detection sensor unit of the system for evaluating illustrated in FIG. 1 to a person.

The myoelectric potential detection sensor unit 30 is a sensor unit attached to the person 11, and detects a myoelectric potential of the skeletal muscle which does not directly act on the driving manipulation performed by the person 11. The myoelectric potential detection sensor unit 30 is attached onto masticatory muscles and mimetic muscles of a face of the person 11. FIG. 2 is a schematic side view for illustrating the position for attaching the detection sensor unit 30 to the person 11. The detection sensor unit 30 includes detection sensor pairs 32, 34, and 36 and an earth electrode 38. The detection sensor pair 32 (32a and 32b) is attached at the position of a masseter muscle of the person 11 to detect the myoelectric potential of the masseter muscle. The detection sensor pair 34 (34a and 34b) is attached at the position of a greater zygomatic muscle of the person 11 to detect the myoelectric potential of the greater zygomatic muscle. The detection sensor pair 36 (36a and 36b) is attached at the position of a glabellar muscle of the person 11 to detect the myoelectric potential of the glabellar muscle.

The masseter muscle does not directly act on the steering operation of the vehicle, which is performed by the person 11. However, when the driver (person 11) performing the steering operation of the vehicle feels heavily stressed or the like, the driver unconsciously "clenches the teeth" due to the stress. As a result, the masseter muscle exhibits a strong activity in some cases. Similarly, the greater zygomatic muscle and the glabellar muscle directly do not act on the steering operation of the vehicle, which is performed by the person 11. However, when the driver performing the steering operation of the vehicle feels heavily stressed or the like, a "change in facial expression" (such as frown) due to the stress unconsciously appears on the driver. As a result, the masseter muscle or the glabellar muscle exhibits a strong activity in some cases. The myoelectric potential detection sensor unit 30 acquires the muscle activity information of each of the plurality of skeletal muscles for each of the cases where the driver is in the relaxing state, where the driver is in the comfortable state due to the stimulus applied by the stimulus application section 24, and where the driver is in the uncomfortable state due to the stimulus applied by the stimulus application section 24.

As a representative of the detection sensor pairs 32, 34, and 36, the detection sensor pair 32 is described. A configuration of each of the detection sensor pairs 34 and 36 is the same as that of the detection sensor pair 32. The detection sensor pair 32 is a sensor for detecting the myoelectric potential of the masseter muscle of the person 11, and includes a pair of the electrodes 32a and 32b corresponding to Ag/AgCL disc electrodes. The pair of disc electrodes (32a and 32b) are attached to a surface of the face of the person 11 at the position of the masseter muscle while being apart from each other by a predetermined distance (for example, 5 mm). A material of the electrodes of the detection sensor pairs 32, 34, and 36 are not limited to Ag/AgCL, and may also be other materials such as Ag or stainless. The electrodes are bonded to the surface of a skin of the person 11 by using an electrode paste after the skin is rubbed with a scrub and then is cleaned with alcohol. At this time, the skin is cleaned until an electric resistance becomes 30 kΩ (desirably, 5 kΩ) or less. The two electrodes are attached to a muscle belly of the muscle to be measured to be parallel to a muscle fiber. In this embodiment, the detection sensor pairs 32, 34, and 36 are bonded to the surface of one side of the face of the person 11.

On the other hand, the electrode 38 is an earth electrode bonded to an earlobe of the person 11, which corresponds to an electrically inactive position, to keep an electric potential of the person 11 constant, and is provided for the accurate measurement with the detection sensor pairs 32, 34, and 36. The detection sensor pairs 32, 34, and 36 are connected by an amplifier and a lead wire, which are not illustrated, to serve as a known operation amplifier for amplifying the myoelectric potential detected by each of the detection sensor pairs 32, 34, and 36. Data of each of the myoelectric potentials which are detected by each of the detection sensor pairs 32, 34, and 36 and amplified is transmitted to the myoelectric potential information acquisition section 26. When functioning in the selection apparatus 12, the myoelectric potential information acquisition section 26 transmits the information of the myoelectric potential transmitted and received from the detection sensor unit 30 to the data processing section 28.

After sampling the time-series data of the myoelectric potential of each of the skeletal muscles, which is acquired in each of the psychological states described above, and performing full-wave rectification thereon, the data processing section 28 performs smoothing processing to generate a myoelectric potential waveform. The data processing section 28 calculates the myoelectric potential intensity from the myoelectric potential waveform to output the calculated myoelectric potential intensity. Here, the myoelectric potential intensity is, for example, a root means square (RMS) value (effective value) of the myoelectric potential waveform, an integrated value (integrated electromyogram (IEMG)) thereof, or the like. Alternatively, for example, when the myoelectric potential data of each of the right and left sides of the person 11 is acquired for the masseter muscle or the greater zygomatic muscle, a simultaneous contraction intensity may be calculated in the following manner. After the time-series data of the myoelectric potential of each of the right and left masseter muscles is sampled to be then subjected to the full-wave rectification, the smoothing processing is performed thereon to generate the smooth myoelectric potential waveform of each of the right and left masseter muscles. From the myoelectric potential waveforms of the right and left masseter muscles, a simultaneous contraction waveform in a predetermined time zone is generated. Then, the simultaneous contraction intensity is calculated from the simultaneous contraction waveform. The simultaneous contraction waveform described herein means a waveform obtained by calculating a geometrical mean value of the values of the myoelectric potentials of the right and left masseter muscles at the same time point or a waveform generated by selecting a smaller one of the values of the myoelectric potentials of the right and left masseter muscles at the same time point. Alternatively, the stress evaluation may be carried out in the following manner. A time-series waveform obtained by rectifying the time-series data of the measured myoelectric potential is normalized by using a maximum myoelectric potential which is preliminarily measured to be recorded and stored, thereby calculating an index. A normalized myoelectric potential waveform obtained by the normalization is generated to be used as the myoelectric potential waveform for the stress evaluation. By normalizing the time-series data of the myoelectric potential by using the maximum myoelectric potential, the effects of the electric resistance of each of the electrodes, which varies each time the myoelectric potential detection sensor unit 30 is bonded, can be reduced. For the evaluation of the stress with higher accuracy in the case where the electrodes are bonded several times, it is preferred to use the normalized myoelectric potential waveform.

The information of the myoelectric potential intensity in each of the psychological states, which is obtained by the data processing section 28, specifically, the information of the myoelectric potential intensity at the time of application of each of the stimuli is stored in the memory 18 in association with information indicating a current stimulus (current state) transmitted from the stimulus control section 22.

The specific skeletal muscle selection section 29 selects the specific skeletal muscle highly sensitive to the psychological state of the person 11 from the skeletal muscles, for which the myoelectric potential intensities have been measured, based on the information of the myoelectric potential intensity in each of the psychological states, which is stored in the memory 18. The muscle working under stress differs for each person. The degree of clenching of the teeth and the degree of frown also differ. For example, even when a plurality of workers feel the same degree of stress, the working muscle among the plurality of muscles and the degree of the activity of the working muscle differ for each person. The specific skeletal muscle selection section 29 selects the muscle having a relatively large amount of change, for example, a relatively large amount of increase in myoelectric potential intensity in the uncomfortable state with respect to the myoelectric potential intensity in the relaxing state and a relatively small amount of increase in myoelectric potential intensity in the comfortable state with respect to the myoelectric potential intensity in the relaxing state as the highly-sensitive skeletal muscle which is affected by the psychological state (in particular, the uncomfortable state under stress) of the person 11.

For example, the muscles, each having the amount of increase (difference) in myoelectric potential intensity in the uncomfortable state with respect to the myoelectric potential intensity in the relaxing state, which is larger than a preset first threshold value, and the amount of increase (difference) in myoelectric potential intensity in the comfortable state with respect to the myoelectric potential intensity in the relaxing state, which is smaller than a preset second threshold value, are first selected. Then, among the selected muscles, the muscle having the largest amount of increase in myoelectric potential intensity in the uncomfortable state with respect to the myoelectric potential intensity in the relaxing state is selected as the specific skeletal muscle. Information of the specific skeletal muscle selected by the specific skeletal muscle selection section 29 is transmitted to a myoelectric potential information selection/acquisition section 42 of the stress evaluation apparatus 14.

The stress evaluation apparatus 14 is an apparatus for evaluating the stress on the driver driving the vehicle at the time of steering of the vehicle. When the stress evaluation apparatus 14 evaluates the stress placed on the person 11 at the time of steering of the vehicle, the driver stimulating mechanism 20 does not apply any stimulus to the person 11. For the evaluation of the stress at the time of steering of the vehicle, the person 11 starts the driving manipulation of the vehicle. Then, the myoelectric potential information acquisition section 26 acquires the information of the myoelectric potential of each of the muscles of the person 11 to transmit the acquired information to the myoelectric potential information selection/acquisition section. The myoelectric potential information selection/acquisition section 42 selects only the myoelectric potential information for the specific skeletal muscle selected by the specific skeletal muscle selection section 29 from the myoelectric potential information of the plurality of skeletal muscles of the person 11 to transmit the selected information of the myoelectric potential of the specific skeletal muscle to the data processing section 44. The specific skeletal muscle selected by the specific skeletal muscle selection section 29 is greatly affected by (highly sensitive to) the psychological state of the person 11 and actively works only when the person 11 is stressed to be in the uncomfortable state. It can be said that the myoelectric potential information of the specific skeletal muscle, which is selected and acquired by the myoelectric potential information selection/acquisition section 42, is highly responsive to the stress felt by the person 11.

The specific skeletal muscle selection section 29 may select the specific skeletal muscle under only one condition that the amount of increase in myoelectric potential intensity in the uncomfortable state with respect to the myoelectric potential intensity in the relaxing state is relatively large. In this case, it is sufficient that the driver stimulating mechanism 20 applies only the stimulus for making the person 11 uncomfortable. Even in this case, the specific skeletal muscle highly sensitive to the stress on the person 11 (the uncomfortable state of the person 11) can be selected from the plurality of skeletal muscles. However, when a relatively large amount of increase in myoelectric potential intensity in the uncomfortable state is the only condition for the selection, a muscle having a relatively large amount of increase in myoelectric potential intensity in the comfortable state is also selected as the specific skeletal muscle. Such a muscle actively works not only when the person 11 is stressed to be in the uncomfortable state but also when the person 11 is brought into the comfortable state. It is not believed that the myoelectric potential information of such a specific skeletal muscle is information corresponding to the stress felt by the person 11 in a one-to-one relation. It is preferred that the specific skeletal muscle selection section 29 select a muscle having a relatively large amount of increase in myoelectric potential intensity in the uncomfortable state with respect to the myoelectric potential intensity in the relaxing state and a relatively small amount of increase in myoelectric potential intensity in the comfortable state with respect to the myoelectric potential intensity in the relaxing state as the specific skeletal-muscle.

The data processing section 44 processes the myoelectric potential information of the specific skeletal muscle, which is selected and acquired by the myoelectric potential information selection/acquisition section 42, to obtain the myoelectric potential intensity while the person 11 is steering the vehicle, as in the case of the data processing section 28 of the selection apparatus 12. For example, as in the case of the data processing section 28, the selected and acquired myoelectric potential information of the specific skeletal muscle is sampled and is then subjected to the full-wave rectification. Thereafter, the smoothing processing is performed to generate the myoelectric potential waveform. From the myoelectric potential waveform, the myoelectric potential intensity is calculated to be output. As in the case of the data processing section 28, it is sufficient that the root means square (RMS) value (effective value) of the myoelectric potential waveform or the integrated value (integrated electromyogram (IEMG)) thereof is calculated as the myoelectric potential intensity.

The stress evaluation section 46 compares, for example, a value of the obtained myoelectric potential intensity with a set value at each of levels which are preset for categorizing the degree of stress in a stepwise manner when the person 11 is performing the driving manipulation, thereby estimating whether the degree of stress placed on the driver 11 when the driver is performing the driving manipulation is high or low. Such a result of evaluation is transmitted together with the myoelectric potential waveform, the myoelectric potential intensity, or the like to an output section 48 formed of a monitor or a printer to be used for display.

Figure 3:
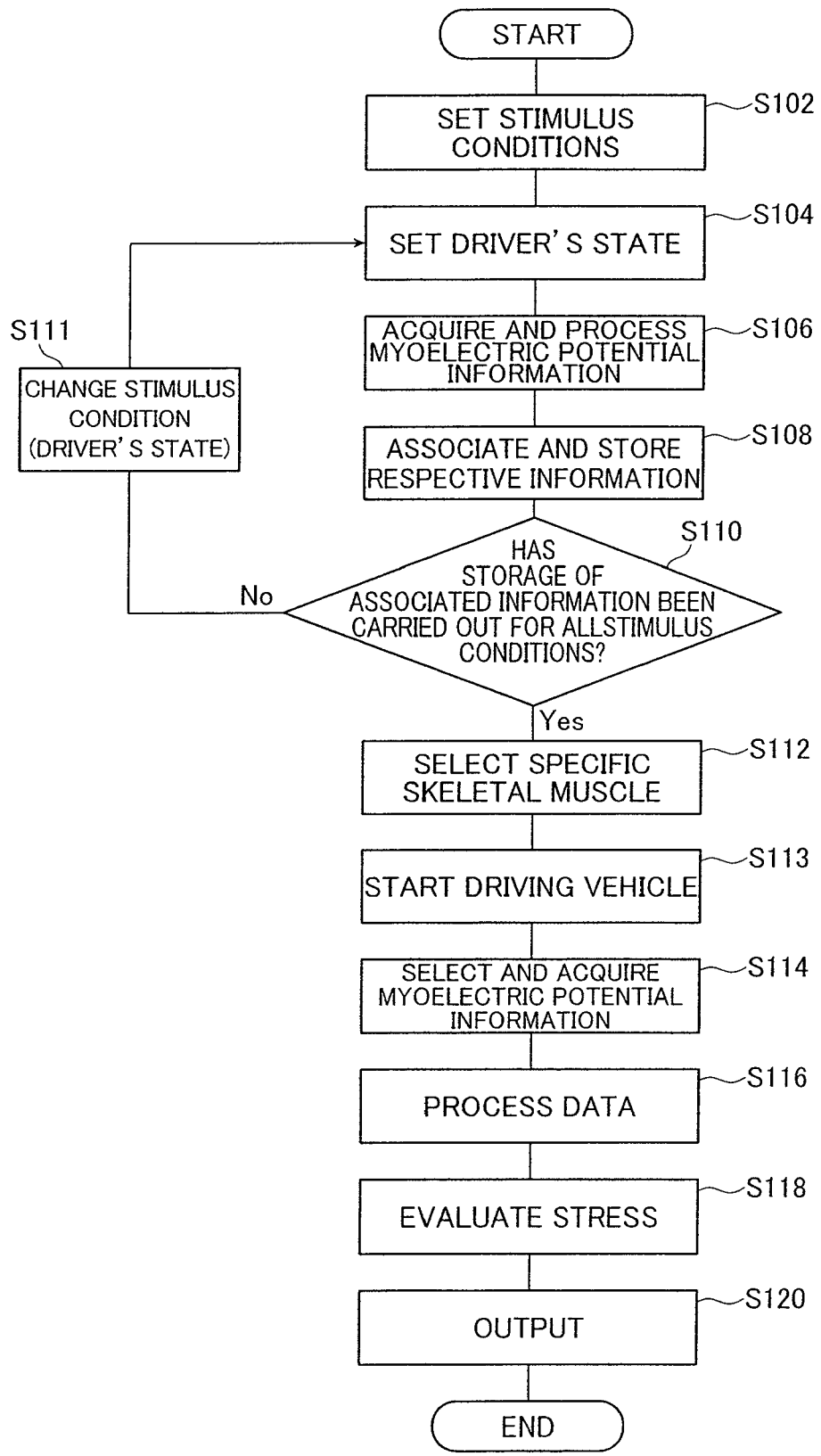
[FIG. 3] This is a flowchart of the first embodiment of a method of evaluating the stress during the operation according to the present invention, which is carried out by using the system for evaluating illustrated in FIG. 1.

The first embodiment of the method of evaluating the stress during the operation, which is carried out in the evaluation system 10 as described above, is specifically described. FIG. 3 is a flowchart of the first embodiment of the method of evaluating the stress during the operation according to the present invention, which is carried out by using the evaluation system 10. The method of evaluating the stress during the operation according to the present invention, which is illustrated in FIG. 3, uses an example of a method of selecting the highly-sensitive skeletal muscles (Steps S102 to S112) according to the present invention. In the method of evaluating the stress during the operation, the specific skeletal muscle of the person 11 is selected. For the selected specific skeletal muscle, the muscle activity information (myoelectric potential intensity) of the specific skeletal muscle while the person 11 is performing the driving manipulation is acquired. Based on the acquired muscle activity information (myoelectric potential intensity), the degree of stress placed on the person 11 while the person 11 is performing the driving manipulation is evaluated.

First, the selection of the specific skeletal muscle of the person 11, which corresponds to an example of the method of selecting the highly-sensitive skeletal muscle according to the present invention, is performed. For the selection of the specific skeletal muscle, conditions of the stimuli to be applied to the person 11 are set (Step S102). Such stimulus conditions are set by an operation of the input means (not shown) such as the keyboard or the mouse by an operator, and are stored in the memory 18 or the like. In this embodiment, three conditions, specifically, a condition in which no stimulus is applied to the person 11 to bring the person 11 into the relaxing state, a condition in which the stimulus for bringing the person 11 into the comfortable state is applied, and a condition in which the stimulus for bringing the person 11 into the uncomfortable state is applied, are set. In this embodiment, the stimulus application section 24 is the aroma generator. As the stimulus for bringing the person 11 into the comfortable state, for example, a condition for releasing the aroma such as a sweet aroma, which makes every common person feel pleasant, is set. On the other hand, as the stimulus for making the person 11 uncomfortable, a condition for releasing the unpleasant odor which makes every common person feel uncomfortable is set.

Next, the stimulus control section 22 controls the operation of the stimulus application section 24 to apply the stimulus to the person 11, thereby setting the state of the person 11 to each of the psychological states described above (Step S104). For example, the stimulus control section 22 controls the operation of the stimulus application section 24 to apply the stimulus according to the stimulus condition prestored and preset in the memory 18 to the person 11, thereby applying the stimulus according to the stimulus condition to the person 11. Here, for setting the state of the person 11 to the relaxing state 11, it is apparent that no stimulus is applied. In this embodiment, the three states, that is, the relaxing state, the comfortable state (state where the sweet aroma is released), and the uncomfortable state (state where the unpleasant odor is released) are sequentially set. In this embodiment, the relaxing state is first set. In this set state, no stimulus (odor) is provided from the stimulus application section 24.

In each of the relaxing state, the comfortable state, and the uncomfortable state, the myoelectric potential information is acquired (Step S106). At this time, the myoelectric potential of each of the masseter muscle, the greater zygomatic muscle and the glabellar muscle of the person 11 is detected by each of the detection sensor pairs (detection sensor pairs 32 to 36) of the myoelectric potential detection sensor unit 30 described above. The data of each of the myoelectric potentials, which is amplified by an amplifier (not shown), is transmitted to the myoelectric potential information acquisition section 26. The myoelectric potential information acquisition section 26 transmits the data of each of the myoelectric potentials to the data processing section 28. After sampling the time-series data of each of the myoelectric potentials and performing the full-wave rectification thereon, the data processing section 28 performs the smoothing processing to generate the myoelectric potential waveform. Then, for example, the myoelectric potential intensity (the RMS value in this embodiment) of each of the myoelectric potential waveforms is calculated to be output. In this embodiment, the time-series waveform obtained by rectifying the time-series data of the measured myoelectric potential is normalized by using the maximum myoelectric potential which is preliminarily measured to be recorded and stored, thereby calculating the index. In this manner, the normalized myoelectric potential waveform is generated to be used.

The information of the myoelectric potential intensity obtained by the data processing section 28 is stored in the memory 18 in association with the information indicating the current stimulus (current state) transmitted from the stimulus control section 22 to be stored in the memory 18 (Step S108). Here, the information of the myoelectric potential intensity acquired for each skeletal muscle is stored in association with the psychological state of the person 11 when the information of the myoelectric potential intensity is acquired. For example, the information of the myoelectric potential intensity of the masseter muscle in the relaxing state, the information of the myoelectric potential intensity of the greater zygomatic muscle in the relaxing state, and the information of the myoelectric potential intensity of the glabellar muscle in the relaxing state, and the like are stored.

After the completion of the storage of the information in association with the psychological state, it is judged whether or not the storage of the information in association with the psychological state has been completed for all the stimulus conditions set in Step S104 (Step S110). When only the myoelectric potential intensity in the relaxing state is stored, it is apparent that the result of judgment in Step S110 is "No". Then, the condition of the stimulus to be applied to the person 11 is changed to change the psychological state to be set for the person 11 (Step S111). In this embodiment, the stimuli are applied to the person 11 in order of, for example, no stimulus, the sweet aroma, and the unpleasant odor. Specifically, in this embodiment, the state of the driver is set in order of, for example, the relaxing state, the comfortable state and the uncomfortable state. The above-mentioned Steps S104 to S111 are repeated, and the information of the myoelectric potential intensity of each of the masseter muscle, the greater zygomatic muscle and the glabellar muscle in the relaxing state, the information of the myoelectric potential intensity of each of the masseter muscle, the greater zygomatic muscle and the glabellar muscle in the comfortable state, and the information of the myoelectric potential intensity of each of the masseter muscle, the greater zygomatic muscle and the glabellar muscle in the uncomfortable state are stored in the memory 18 in association with each of the states.

Next, the specific skeletal muscle selection section 29 selects the specific skeletal muscle of the person 11, which is highly sensitive to the psychological state of the person 11, based on the myoelectric potential information in each of the psychological states, which is stored in the memory 18 (Step S112). The specific skeletal muscle selection section 29 selects as the specific skeletal muscle a muscle having a relatively large amount of increase in myoelectric potential intensity in the uncomfortable state with respect to the myoelectric potential intensity in the relaxing state and a relatively small amount of increase in myoelectric potential intensity in the comfortable state with respect to the myoelectric potential intensity in the relaxing state.

FIGS. 4(a) and 4(b) are graphs, each illustrating the degree of sensitivity of each of the plurality of skeletal muscles of the person to the psychological state of the person, which is obtained by carrying out the stress evaluation method according to this embodiment. More specifically, the myoelectric potential intensity (in % MVC in this case) of each of the plurality of skeletal muscles of the driver in each of the states where the sweet aroma is provided to the driver (the driver is brought into the comfortable state), where no stimulus is applied to the driver (the driver is in the relaxing state), and where the unpleasant odor is provided to the driver (the driver is brought into the uncomfortable state) is illustrated. FIGS. 4(a) and 4(b) illustrate the results for different persons.

For a person A illustrated in FIG. 4(a), each of the masseter muscle and the glabellar muscle has the amount of increase (difference) in myoelectric potential intensity in the uncomfortable state with respect to the myoelectric potential intensity in the relaxing state larger than a preset first threshold value. However, the glabellar muscle of the person A has the amount of increase (difference) in myoelectric potential intensity in the comfortable state with respect to the myoelectric potential intensity in the relaxing state larger than a preset second threshold value. For the person A, only the masseter muscle has the above-mentioned amount of increase (difference) in myoelectric potential intensity in the uncomfortable state larger than the first threshold value, and the above-mentioned amount of increase (difference) in myoelectric potential intensity in the comfortable state with respect to the myoelectric potential intensity in the relaxing state smaller than the preset second threshold value. For such a person A, the masseter muscle is selected as the specific skeletal muscle.

On the other hand, for a person B illustrated in FIG. 4(b), each of the masseter muscle and the glabellar muscle has the amount of increase (difference) in myoelectric potential intensity in the uncomfortable state with respect to the myoelectric potential intensity in the relaxing state larger than the preset first threshold value. However, the masseter muscle of the person B has the amount of increase (difference) in myoelectric potential intensity in the comfortable state with respect to the myoelectric potential intensity in the relaxing state larger than the preset second threshold value. For the person B, only the glabellar muscle has the above-mentioned amount of increase (difference) in myoelectric potential intensity in the uncomfortable state larger than the first threshold value, and the above-mentioned amount of increase (difference) in myoelectric potential intensity in the comfortable state with respect to the myoelectric potential intensity in the relaxing state smaller than the preset second threshold value. For such a person B, the glabellar muscle is selected as the specific skeletal muscle.

As in each of the examples illustrated in FIGS. 4(a) and 4(b), the skeletal muscle reacting to the stress differs for each person. Some muscles work in the same way regardless of whether the person is in the uncomfortable state or in the comfortable state. Such muscles work when the person is psychologically stressed, but also work even when the person feels pleasant. In this embodiment, the stimulus for bringing the driver into the uncomfortable state as well as the stimulus for bringing the driver into the comfortable state are applied to the subject (driver) to obtain the muscle activity information of each of the muscles in the respective states. Then, the muscle which exclusively works in response to the stimulus for bringing the driver into the uncomfortable state and does not actively work in response to the stimulus for bringing the driver into the comfortable state is selected as the specific skeletal muscle which is highly sensitive to the psychological state of the driver. The information of the specific skeletal muscle selected by the specific skeletal muscle selection section 29 is transmitted to the myoelectric potential information selection/acquisition section 42 of the stress evaluation apparatus 14.

The driving of the vehicle is started by the person 11 with the specific skeletal muscle being selected (Step S113). In this embodiment, the stress generated on the person A when the person A illustrated in FIG. 4(a) drives and manipulates the vehicle is evaluated. In this embodiment, the person 11 (person A) drives the vehicle to run a predetermined specific driving course, for example, as illustrated in FIG. 5, under specific driving conditions. FIG. 5 is a schematic top view illustrating the driving course of the vehicle driven and manipulated by the person, in the stress evaluation method according to the first embodiment (and a second embodiment described below). The evaluation system 10 (in particular, the evaluation apparatus 14) evaluates the degree of stress to which the person 11 is subjected at this time. The driving course illustrated in FIG. 5 is a driving course with a so-called lane change. The person 11 drives the vehicle to run through a route along a directional line illustrated in the drawing while passing between objects (pylons) placed on a road surface.

While the person 11 is driving the vehicle to run the driving course illustrated in FIG. 5, the driver stimulation mechanism 20 does not apply any stimulus to the person 11. While the vehicle is driving the running course illustrated in FIG. 5 after the person 11 starts the driving manipulation of the vehicle, the myoelectric potential information acquisition section 26 acquires the information of the myoelectric potential of each of the above-mentioned muscles of the person 11 to transmit the acquired information to the myoelectric potential information selection/acquisition section. The myoelectric potential information selection/acquisition section 42 selects and acquires only the myoelectric potential information for the specific skeletal muscle (masseter muscle in the case of the person 11 (person A)) selected by the specific skeletal muscle selection section 29 from the respective myoelectric potential information of the plurality of skeletal muscles of the person 11 (Step S114). For the person 11, the masseter muscle selected by the specific skeletal muscle selection section 29 is a muscle which is highly sensitive to the psychological state of the person 11 and actively works only when the person is subjected to the stress. The myoelectric potential information of the specific skeletal muscle selected and acquired by the myoelectric potential information selection/acquisition section 42 is highly responsive to the stress felt by the person 11.

The myoelectric potential information selection/acquisition section 42 transmits the selected information of the myoelectric potential of the masseter muscle to the data processing section 44. Similarly to the data processing section 28 of the selection apparatus 12, the data processing section 44 processes the myoelectric potential information of the specific skeletal muscle, which is selected and acquired by the myoelectric potential information selection/acquisition section 42, to obtain the myoelectric potential intensity while the person 11 is steering the vehicle (Step S116).

Figure 6:
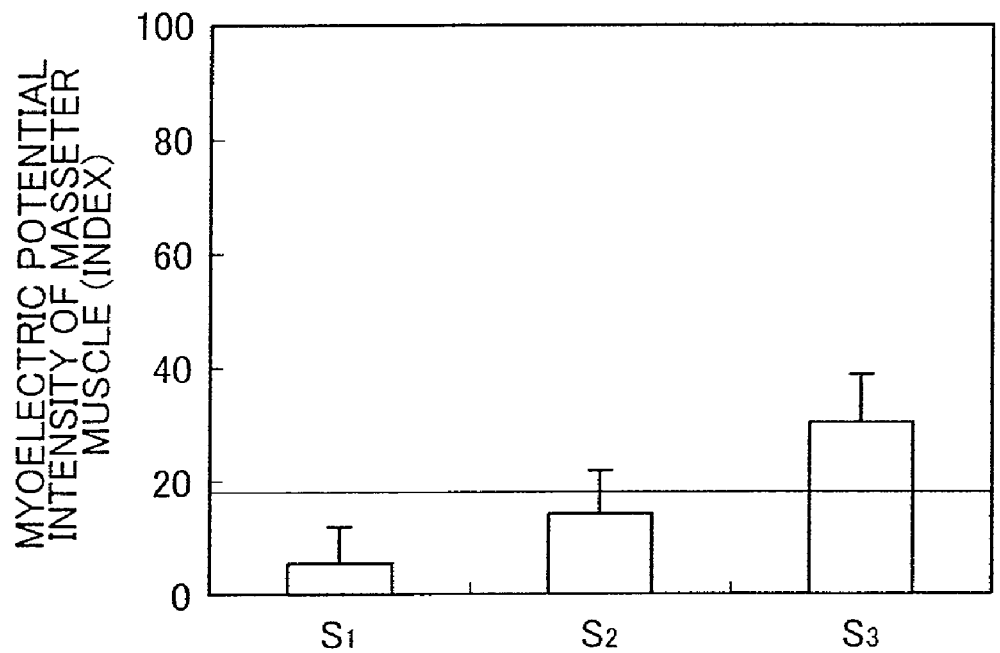
[FIG. 6] This is a graph illustrating an example of degree of stress on the person during the operation, which is output by the method of evaluating the stress according to the first embodiment.

Then, the stress evaluation section 46 evaluates the degree of stress placed on the person 11 during the driving manipulation (Step S118). For example, a value of the obtained myoelectric potential intensity is compared with the respective levels of the set value, which are preset for categorizing the degree of stress placed on the subject during the operation in a stepwise manner, thereby evaluating the degree of stress placed on the subject during the operation. A result of such evaluation is transmitted together with the myoelectric potential waveform, the myoelectric potential intensity and the like to the output section 48 formed of the monitor or the printer to be used for display (Step S120). FIG. 6 is an example of a graph illustrating the degree of the stress placed on the person 11 during the operation, which is output by the stress evaluation method according to this embodiment. FIG. 6 is a graph of the evaluation value representing the degree of stress placed on the person 11 while the person 11 is driving and manipulating vehicles ($S_1$, $S_2$, and $S_3$) respectively having three different vehicle characteristics. In the example illustrated in FIG. 6, as the evaluation value representing the degree of stress, the value (index) obtained by normalizing the myoelectric potential intensity (RMS value) of the specific skeletal muscle (masseter muscle) of the person 11 by using the maximum myoelectric potential is used. Differences in vehicle characteristic between the three vehicles ($S_1$, $S_2$, and $S_3$) result from differences between the types of tires to be mounted.

In this embodiment, an index value of the myoelectric potential intensity is preset as the threshold value (is prestored in the memory 18). When the index value of the myoelectric potential intensity becomes greater than the threshold value, the stress evaluation section 46 judges that the specific skeletal muscle of the person excessively work and the person 11 is excessively stressed. When the vehicle $S_3$ of the three vehicles ($S_1$, $S_2$, and $S_3$) is driven, the index value of the myoelectric potential intensity of the person 11 becomes greater than the preset threshold value. Therefore, the stress evaluation section 46 judges that the person 11 is excessively stressed. For example, as the result of evaluation for the case where the vehicle $S_3$ is driven, the output section 48 displays and outputs a text for notifying the result of judgment such as "an excessive stress is placed" together with the value of the index as described above. Further, as in the case where the stress during the operation is evaluated for each of the plurality of conditions, it is preferred to display and output a graph for comparing the results of evaluation for the respective conditions as illustrated in FIG. 6. From the graph illustrated in FIG. 6, it is understood that the most stressless vehicle for the person 11, that is, the vehicle which is the easiest to drive is the vehicle $S_1$. The second easiest vehicle to drive is the vehicle $S_2$, and the vehicle $S_3$ is the hardest to drive. From such results, the degree of easiness in driving can be qualitatively and quantitatively identified for the tire mounted to the vehicle.

Figure 7:
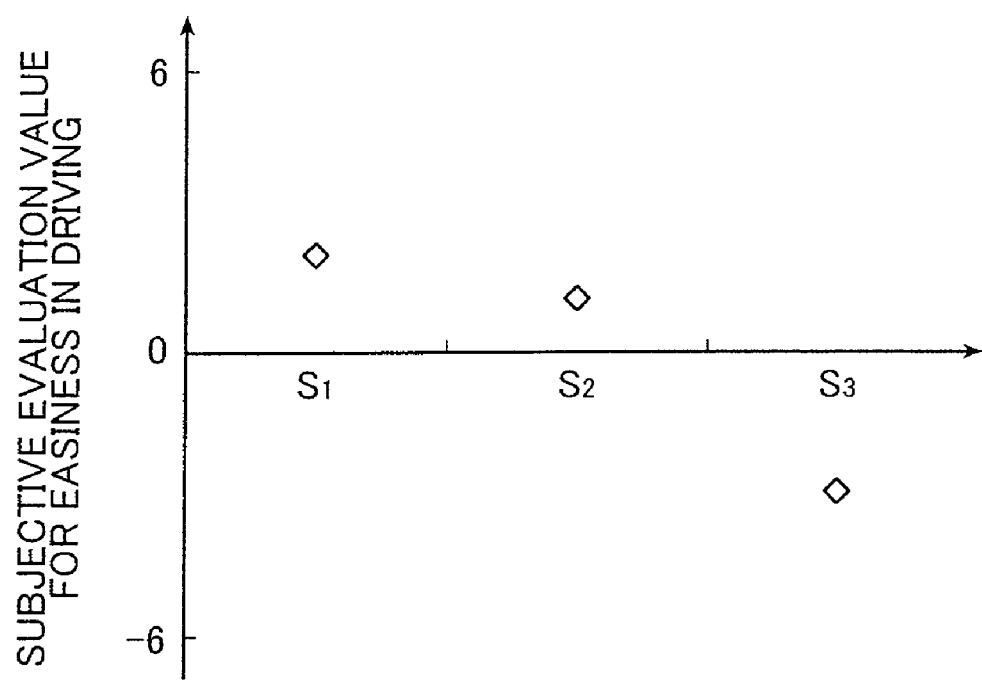
[FIG. 7] This is a graph illustrating results of a subjective evaluation experiment on the person.

FIG. 7 is a graph illustrating the result of a subjective evaluation experiment on the person, which is carried out for verifying the effects of the method of evaluating the stress during the operation according to the present invention. More specifically, FIG. 7 illustrates the degree of easiness in driving, which is felt by the person 11 when the person 11 drives each of the vehicles $S_1$ to $S_3$ to run on the course illustrated in FIG. 5. The degree of easiness in driving, which is felt by the person 11, is digitized by a sensory evaluation using a so-called interval scale, in which the person 11 himself (or herself) designates the degree of easiness in driving with a numerical value (the easiness in driving becomes higher as a positive absolute value increases, whereas the difficulty in driving become higher as a negative absolute value increases). As illustrated in FIG. 7, the easiest vehicle to drive for the person 11 is the vehicle $S_1$, the second easiest vehicle to drive is the vehicle $S_2$, and the most difficult vehicle to drive is the vehicle $S_3$. In addition, the person 11 subjectively feels that only the vehicle $S_3$ is hard to drive. Specifically, only when the vehicle $S_3$ is driven, an excessive stress is placed on the person 11. The result of the subjective evaluation experiment illustrated in FIG. 7 well corresponds to the result of the method of evaluating the stress during the operation according to the present invention, which is illustrated in FIG. 6. By using the method of evaluating the stress during the operation according to the present invention, the degree of stress to which the person is subjected during the operation can be quantitatively evaluated with high accuracy.

Figure 8:
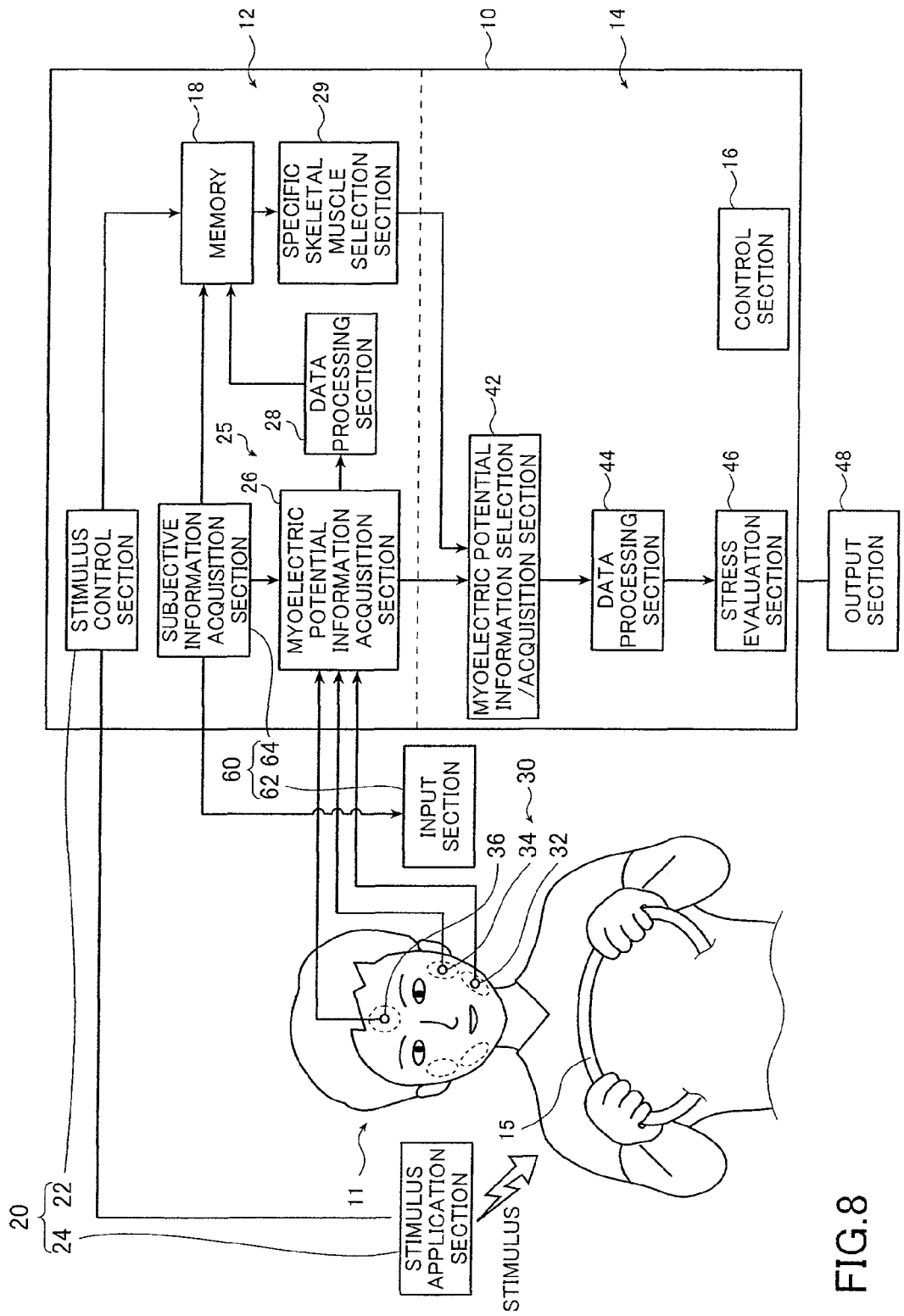
[FIG. 8] This is a schematic configuration diagram for illustrating an example of the second embodiment of the system for evaluating the stress during the operation according to the present invention.

Next, a second embodiment of the present invention is described. FIG. 8 is a schematic configuration diagram for illustrating an evaluation system 50 corresponding to the second embodiment of the system for evaluating the stress during the operation according to the present invention. The evaluation system 50 according to the second embodiment of the present invention differs from the evaluation system 10 according to the first embodiment of the present invention in that a subjective information acquisition mechanism 60 is included. The subjective information acquisition mechanism 60 includes an input section 62 formed of a mouse, a keyboard, and the like, which is subjected to an input operation performed by the person 11, and a subjective information acquisition section 64 for acquiring subjective information of the person 11, which is input with the input section 62.

The second embodiment is suitably used when, for example, the state of the person 11 cannot be clearly defined by the stimulus applied by the stimulus application section 24 as in the case of the application of a pain stimulus to the person 11 and the like. As in the case where the pain stimulus is applied to the person 11 by using, for example, a known finger-pressure device with an adjustable finger pressure as the stimulus application section 24, the finger pressure with the finger-pressure device brings the person 11 into the comfortable state in some cases and into the uncomfortable state in the other cases. A criterion of the degree of finger pressure for bringing the person into the comfortable state or the degree of finger pressure for bringing the person into the uncomfortable state differs for each person. In the second embodiment, the subjective information acquisition section 64 applies the stimulus from the stimulus application section 24 to the person 11, and in addition, acquires the subjective information indicating the current psychological state of the person 11 by input of the subjective information by the person 11 himself (or herself). The subjective information indicating the current psychological state of the person 11, which is acquired by the subjective information acquisition section 64, is stored in the memory 18 in association with information of the current stimulus applied to the person 11 (current psychological state), which is transmitted from the stimulus control section 22, and information of the current myoelectric potential intensity of the person 11, which is transmitted from the data processing section. The specific skeletal muscle selection section 29 selects the specific skeletal muscle of the person 11 based on the above-mentioned information which is respectively associated with each other. Hereinafter, the second embodiment of the system for evaluating the stress during the operation according to the present invention, which is carried out by using the evaluation system 50 according to the second embodiment of the present invention, is described. In the following description, the same components as those of the evaluation system 10 according to the first embodiment are described by using the same reference numerals as those used in the description of the first embodiment.

Figure 9:
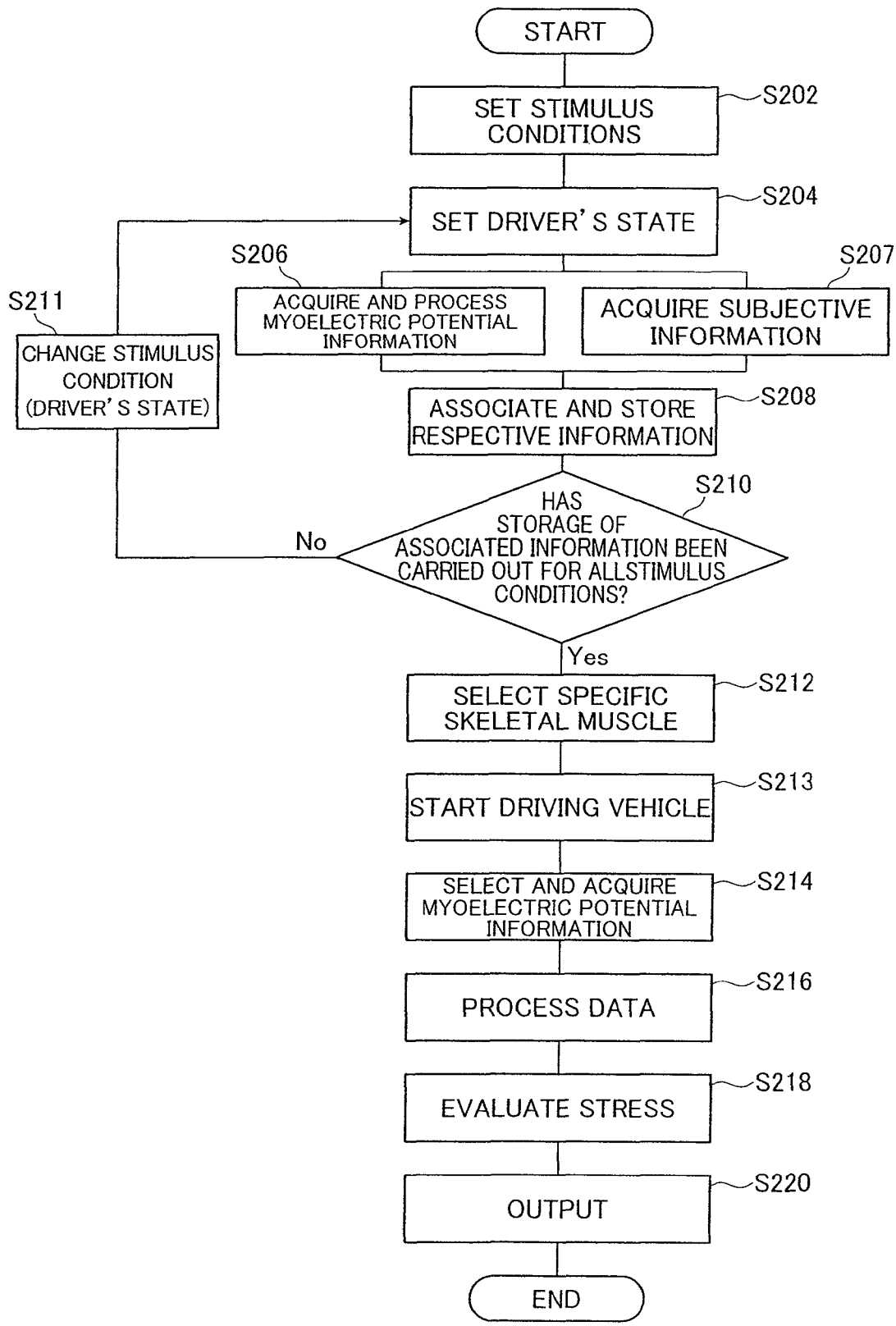
[FIG. 9] This is a flowchart of the second embodiment of the method of evaluating the stress during the operation according to the present invention, which is carried out by using the system for evaluating illustrated in FIG. 8.

FIG. 9 is a flowchart of the second embodiment of the method of evaluating the stress during the operation according to the present invention. In the method of evaluating the stress during the operation illustrated in FIG. 9, the specific skeletal muscle of the person 11 is selected by the second embodiment of the method of selecting the highly-sensitive skeletal muscle (Steps S202 to S212) according to the present invention. Then, the muscle activity information (myoelectric potential intensity) of the selected specific skeletal muscle during the steering operation performed by the person 11 is acquired. Based on the acquired muscle activity information (myoelectric potential intensity) of the specific skeletal muscle, the degree of stress placed on the person 11 during the steering operation is evaluated.

First, the highly-sensitive skeletal muscle (specific skeletal muscle) of the person 11 is selected. As in the first embodiment, the condition of the stimulus to be applied to the person 11 is set for the selection of the highly-sensitive skeletal muscle (Step S202). Such a stimulus condition is set by operating the input means (not shown) such as the keyboard or the mouse by the operator to be stored in the memory 18 or the like. In this embodiment, a condition in which the pain stimulus is applied to the person 11 by the finger pressure is set. As the finger pressure, in addition to a condition for bringing the person 11 into the relaxing state without any application of the finger pressure, ten different levels of finger pressure are set. It is apparent which level of finger pressure brings the person 11 into the comfortable state or which level of finger pressure brings the person 11 into the uncomfortable state is still unknown at the end of this step.

Next, the stimulus control section 22 controls the operation of the stimulus application section 24 to apply the pain stimulus to the person 11 (Step S204). For example, the stimulus control section 22 controls the operation of the stimulus application section 24 to apply the stimulus according to the stimulus condition stored in advance and preset in the memory 18 to the person 11, thereby applying the stimulus according to the stimulus condition to the person 11. Here, for setting the state of the person 11 to the relaxing state, it is apparent that no stimulus is applied. In this embodiment, from the relaxing state, the level of setting of the stimulating finger pressure is gradually increased. In this embodiment, the relaxing state is first set.

Then, in each of the states where the respective levels of the stimulus are applied, the myoelectric potential information is acquired (Step S206). At this time, the myoelectric potential of each of the masseter muscle, the greater zygomatic muscle, and the glabellar muscle of the person 11 is detected by each of the detection sensor pairs (detection sensor pairs 32 to 36) of the myoelectric potential detection sensor unit 30 described above. The data of each of the myoelectric potentials, which is amplified by an amplifier (not shown), is transmitted to the myoelectric potential information acquisition section 26. The myoelectric potential information acquisition section 26 transmits the data of each of the myoelectric potentials to the data processing section 28. After sampling the time-series data of each of the myoelectric potentials and performing the full-wave rectification thereon, the data processing section 28 performs the smoothing processing to generate the myoelectric potential waveform. Then, the myoelectric potential intensity of each of the myoelectric potential waveforms is calculated to be output.

In this second embodiment, the myoelectric potential information is acquired in each of the states where the respective levels of the stimulus are applied. In addition, the subjective information indicating the current state of the person 11 is acquired (Step S207). The subjective information is input by the person 11 himself (or herself) by using the input section 62 to be acquired by the subjective information acquisition section 64. For example, when the person 11 feels pleasant (specifically, is in the comfortable state), the person 11 is invited to input a positive value according to the degree of comfort (as a positive absolute value becomes greater, the comfort is greater). When the person 11 feels painful (specifically, is in the uncomfortable state), the person 11 is invited to input a negative value according to the degree of pain (as a negative absolute value becomes greater, the pain is greater). In this manner, subjective evaluation values (subjective information) indicating the degree of comfort (comfortable state) and the degree of pain (uncomfortable state), which are numerically represented by a so-called SD method, are acquired by the subjective information acquisition section 64.

The information of the myoelectric potential intensity obtained by the data processing section 28 and the subjective information of the person 11, which is acquired by the subjective information acquisition section 64, are stored in the memory 18 in association with the information indicating the current degree of stimulus (current state), which is transmitted from the stimulus control section 22 (Step S208). When the association and the storage in the memory 18 are completed, it is judged whether or not the association and the storage in the memory 18 have been completed for all the stimulus conditions set in Step S204 (Step S210). When not all the levels of stimulus are applied yet, the result of judgment in this Step S210 is "No". Then, the condition of the stimulus applied to the person 11 is changed to change the state of the person 11 (Step S211). The processing in Steps S204 to S210 is repeatedly implemented until the result of judgment in Step S210 becomes "Yes".

Figure 10:
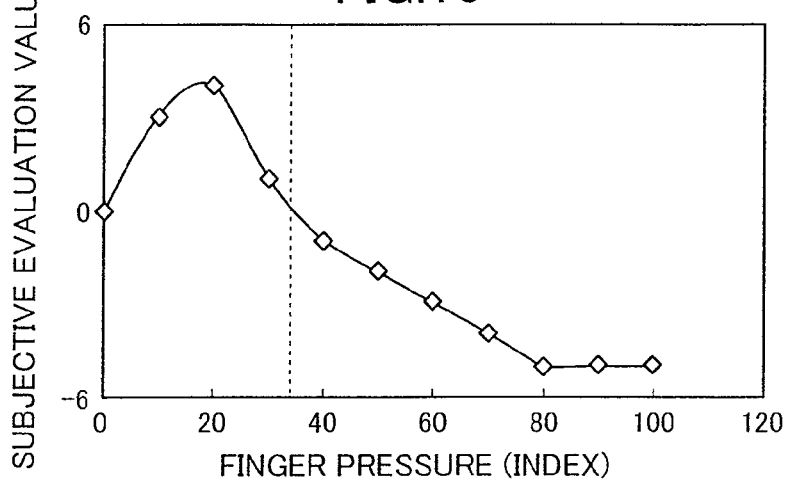
[FIG. 10] This is a graph illustrating a relation between a subjective evaluation value and a finger pressure, which is acquired by the method of evaluating the stress according to the second embodiment.
Figure 11:
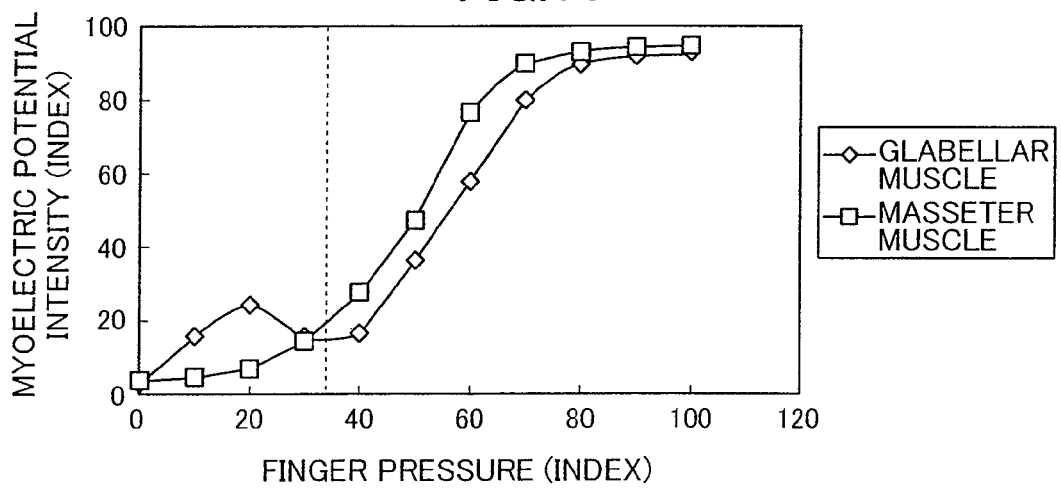
[FIG. 11] This is a graph illustrating a relation between a myoelectric potential intensity and the finger pressure, which is acquired by the method of evaluating the stress according to the second embodiment.

FIG. 10 is a graph illustrating the relation between the subjective information and the finger pressure, which is acquired in this second embodiment. FIG. 11 is a graph illustrating the relation between the myoelectric potential intensity (index) and the finger pressure, which is acquired in this second embodiment. In FIG. 11, a variation in myoelectric potential intensity with a change in finger pressure is illustrated for each of the masseter muscle and the glabellar muscle of the person 11. In FIG. 10, each level of finger pressure is represented by an index with a maximum finger pressure of 100. In this example, as described above, the information of the myoelectric potential intensity and the information indicating the current degree of stimulus (finger pressure) are associated with each other and the subjective information (subjective evaluation value) and the information indicating the current degree of stimulus (finger pressure) are associated with each other to be stored in the memory 18.

Next, the specific skeletal muscle selection section 29 selects the specific skeletal muscle of the person 11, which is highly sensitive to the psychological state of the person 11, based on the subjective information and the myoelectric potential information in each of the states, which are stored in the memory 18 (Step S212). The specific skeletal muscle selection section 29 selects a muscle having a relatively large amount of increase in myoelectric potential intensity in the uncomfortable state with respect to the myoelectric potential intensity in the relaxing state and a relatively small amount of increase in myoelectric potential intensity in the comfortable state with respect to the myoelectric potential intensity in the relaxing state as the specific skeletal muscle. At this time, based on the subjective information (subjective evaluation value) of the person 11, the specific skeletal muscle selection section 29 specifies the state of the person 11 when each subjective information is acquired to thereby specify the state of the person 11 when each muscle activity information corresponding to each subjective information is acquired.

In the example illustrated in FIG. 10, it is understood that the person 11 feels pleasant (is in the comfortable state) when the applied finger pressure is less than about 35 and feels painful (uncomfortable) when the applied finger pressure is greater than about 35. As described above, from the graph of FIG. 10, it is understood that the uncomfortable state is provided when the applied finger pressure is less than about 35 and a peak in the comfortable state (comfort peak) is obtained when the finger pressure (index) is about 19. Specifically, based on the subjective information (subjective evaluation value) of the person 11, the psychological state of the person 11 when each subjective information is acquired can be specified. The specified psychological state of the person 11 corresponds to the psychological state of the person 11 when each muscle activity information corresponding to each subjective information is acquired. The graph of FIG. 11 illustrates that the myoelectric potential intensity becomes greater as the state of the person 11 becomes more uncomfortable (as the person feels more pain) in an area with the finger pressure of greater than about 35, for the masseter muscle. In addition, for the masseter muscle, within an area with the finger pressure of less than about 35, even when the state of the person 11 becomes comfortable, the myoelectric potential intensity scarcely varies even in an area with the finger pressure (index) of about 19. It can be said that the masseter muscle is suitable for the person 11 as the specific skeletal muscle of the person 11, which is highly sensitive to the psychological state of the person 11. On the other hand, as seen from the graph of FIG. 11, for the glabellar muscle, the myoelectric potential intensity becomes greater as the state of the person 11 becomes more uncomfortable (as the person feels more pain) in the area with the finger pressure of greater than about 35. For the glabellar muscle, however, the myoelectric potential intensity becomes greater even in the area with the finger pressure (index) of about 19 in which the degree of the comfortable state of the person 11 has a peak, within the area with the finger pressure of less than about 35. Specifically, for the person 11, the glabellar muscle works not only when the person 11 is psychologically stressed but also when the person 11 feels pleasant. As compared with the masseter muscle, the glabellar muscle is less suitable as the specific skeletal muscle for the person 11. As described above, the masseter muscle is more suitable as the specific skeletal muscle than the glabellar muscle for the person 11. In the second embodiment, even when it is difficult to clearly define the psychological state of the person 11 by the stimulus applied by the stimulus application section 24 as in the case of the application of the pain stimulus to the person 11, the highly-sensitive skeletal muscle can be selected with high accuracy for each person.

The information of the specific skeletal muscle selected by the specific skeletal muscle selection section 29 is transmitted to the myoelectric potential information selection/acquisition section 42 of the stress evaluation apparatus 14. With the specific skeletal muscle being selected in this manner, the driving of the vehicle is started by the person 11 (Step S213). Hereinafter, as in the first embodiment, the stress placed on the person 11 during the operation is evaluated based on the myoelectric potential intensity information of the specific skeletal muscle selected by the specific skeletal muscle selection section 29. The subsequent Steps S214 to S220 are carried out in the same manner as in the case of Steps S114 to S120 of the first embodiment. For the subsequent steps in the second embodiment, the detailed description is herein omitted.

Figure 12:
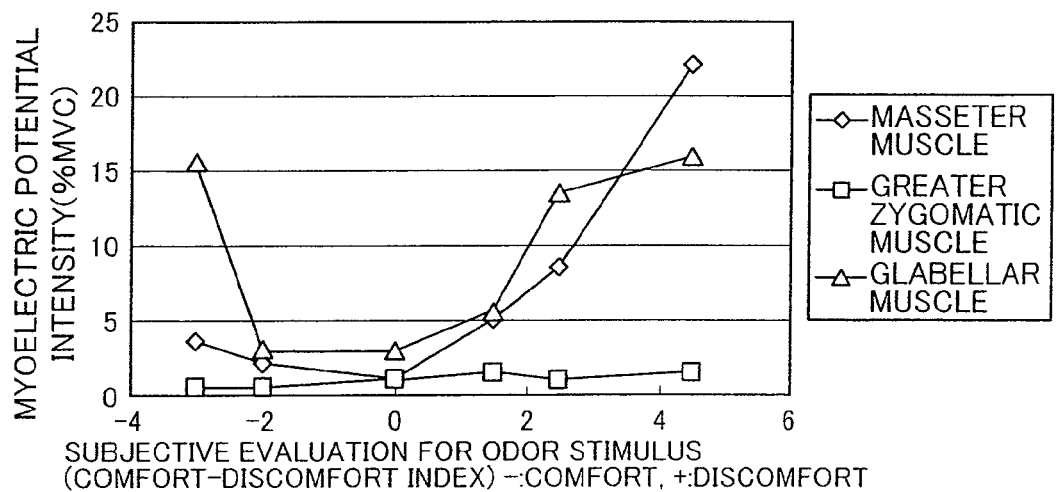
[FIG. 12] This is a graph illustrating a relation between the myoelectric potential intensity and a subjective evaluation for an odor when an odor stimulus is applied from a stimulus application section in the system for evaluating illustrated in FIG. 8.

Even when the state of the person 11 can be clearly defined by the stimulus applied by the stimulus application section 24 as in the case where, for example, an aroma is released to bring the person 11 into the comfortable state or a distinct unpleasant odor is released to bring the person 11 into the uncomfortable state (the stimulus forcibly brings the person into the uncomfortable state), the second embodiment of the present invention may be used to select the specific skeletal muscle. FIG. 12 is a graph illustrating the relation between the myoelectric potential intensity (index) and the subjective evaluation for the odor when an odor stimulus is released from the stimulus application section 24 in the evaluation system 50 illustrated in FIG. 8. In this embodiment, even when the state of the person 11 can be clearly defined by the stimulus applied by the stimulus application section 24 as described above, the degree of the psychological state of the person, which corresponds to the degree of stimulus, is quantified by the subjective evaluation. As a result, the degree of stress indicated by a muscle tension of the specific skeletal muscle can be quantified with higher accuracy for the evaluation. For example, even when the sensitivity to the stimulus such as the odor stimulus or the pain stimulus greatly varies for each person, the subjective evaluation value for the stimulus is acquired. As a result, a numerical value indicating the degree of stimulus can be indicated as a numerical value indicating the degree of the comfortable state or the uncomfortable state of each person. As a result, as shown on the graph illustrated in FIG. 12, the numerical information of the myoelectric potential intensity according to the degree of stimulus and the numerical information indicating the degree of the comfortable state or the uncomfortable state can be shown in association with each other with good accuracy.

According to the method of evaluating the stress during the operation according to the present invention as described above, the muscle suitable for the evaluation of the stress during the operation based on the muscle activity is selected for each person to quantitatively evaluate the stress during the operation with high accuracy for each person. As a result, the degree of stress placed on the worker during the operation can be quantitatively evaluated with relatively high accuracy. For example, the stress to which the driver driving the vehicle is subjected can be quantitatively evaluated with high accuracy. For example, in the case where a plurality of different sets of tires are mounted to a specific vehicle, the stress to which a specific driver is subjected when the specific driver continuously drives the specific vehicle for a long time can be quantitatively evaluated with high accuracy. Thus, the driver can quantitatively know with high accuracy which set of tires provides which degree of indefatigability for driving. By using such information, the tire which is less stressful for the driver, specifically, the tire which hardly fatigues the driver can be efficiently developed. By using the present invention, a detailed relation of the stress on the driver not only with the tires but also with various conditions such as the vehicle, a vehicle control system, and environments (including road design, road surface, and weather) can be easily identified.

In the first and second embodiments described above, among the plurality of skeletal muscles of the person, the muscle having a relatively large amount of increase in muscle activity information in the uncomfortable state of the person with respect to the muscle activity information in the relaxing state of the person (the amount of increase larger than the set threshold value) is selected as the specific skeletal muscle. In the present invention, the criterion for the selection of the specific skeletal muscle is not limited to such a mode. For example, based only on the degree of myoelectric potential intensity when the person is brought into the uncomfortable state by the application of the stimulus, the muscle having a relatively large myoelectric potential intensity (greater than the set threshold value) may be selected as the specific skeletal muscle. Moreover, based on a rate of change in myoelectric potential intensity while the stimulus is being applied to the person, the muscle having a relatively small rate of change (smaller than the set threshold value) may be selected as the specific skeletal muscle. Further, based on a variation in myoelectric potential intensity when the stimulus is repeatedly applied to the person, the muscle having a relatively small variation (smaller than the set threshold value) may be selected as the specific skeletal muscle.

In the present invention, it is preferred to apply the stimulus to a sense organ necessary for the operation of evaluating the stress among the sense organs of the person. For example, when it is believed that the worker is stressed by the odor during the operation, it is preferred to select the specific skeletal muscle based on the muscle activity information obtained with the stimulus to an olfactory sense.

Further, in the first and second embodiments described above, among the plurality of skeletal muscles of the person, the muscle activity information is measured for the masticatory muscles (masseter muscle) and the mimetic muscles (greater zygomatic muscle and glabellar muscle) of the face. Based on the muscle activity information, the specific skeletal muscle is selected from the masticatory muscles and the mimetic muscles of the face. In the present invention, the specific skeletal muscle to be selected is not particularly limited, and may be any skeletal muscle as long as it is not directly related with a target operation for which the stress is to be evaluated. When the operation to be evaluated involves an action, it is sufficient that the skeletal muscles having a low degree of relationship with the action for the operation are specified and the specific skeletal muscle is selected from the specified skeletal muscles. At this time, it is sufficient that the skeletal muscle which is not directly related with (has a low degree of relationship with) the target operation is specified by using the myoelectric potential waveform obtained by an electromyography, the result of simulation using a musculoskeletal model, or the like. At this time, the subject actually may perform the operation to measure the myoelectric potential information generated with the operation. In addition, action information (such as articular angle information) may be acquired by the analysis of an image photographed by a camera, the analysis of information acquired by motion capture or the like.

The method and the apparatus for selecting the specific skeletal muscle, the method of evaluating the stress during the operation, and the system for evaluating the stress during the operation have been specifically described. However, the present invention is not limited to the embodiments described above. It is apparent that various modifications and changes are possible without departing from the gist of the present invention.

The invention claimed is:

1. A method of selecting a specific skeletal muscle affected by a psychological state of a person from a plurality of skeletal muscles of the person in order to evaluate a stress on the person during an operation, comprising:
   a step of applying at least a first stimulus directly to at least one sense organ of the person with an external stimulus applying means to bring the person into an uncomfortable state, the first stimulus being different from a stimulus applied to the person during the operation in which the stress is evaluated;
   a step of acquiring muscle activity information of each of the plurality of skeletal muscles of the person when the first stimulus is applied to the person; and
   a step of selecting the specific skeletal muscle based on the muscle activity information of each of the plurality of skeletal muscles of the person when the person is brought into the uncomfortable state by the first stimulus.

2. The method of selecting the specific skeletal muscle according to claim 1, further comprising:
   a step of acquiring the muscle activity information of each of the plurality of skeletal muscles of the person when the person is in a relaxing state, prior to the step of selecting the specific skeletal muscle,
   wherein a muscle having a larger amount of change in the muscle activity information when the person is brought into the uncomfortable state by the first stimulus with respect to the muscle activity information in the relaxing state as compared with a set first threshold value is selected as the specific skeletal muscle from the plurality of skeletal muscles of the person in the selecting step.

3. The method of selecting the specific skeletal muscle according to claim 2, wherein:
a plurality of stimuli including the first stimulus for bringing the person into the uncomfortable state and a second stimulus for bringing the person into a comfortable state are sequentially applied in the step of applying the stimulus to the person; and
a muscle having the larger amount of change in the muscle activity information when the person is brought into the uncomfortable state by the first stimulus with respect to the muscle activity information in the relaxing state as compared with the set first threshold value and a smaller amount of change in the muscle activity information when the person is brought into the comfortable state by the second stimulus with respect to the muscle activity information in the relaxing state as compared with a set second threshold value is selected as the specific skeletal muscle in the selecting step.

4. The method of selecting the specific skeletal muscle according to claim 1, wherein:
the muscle activity information of each of the plurality of skeletal muscles of the person is acquired for the each stimulus when the each stimulus is applied to the person, while subjective evaluation information of the person indicating the psychological state of the person at this time is acquired, in the step of acquiring the muscle activity information; and
the psychological state of the person when the each subjective evaluation information is acquired is specified based on the subjective evaluation information of the person in the selecting step.

5. The method of selecting the specific skeletal muscle according to claim 4, wherein:
a plurality of different stimuli are sequentially applied to the person in the step of applying the stimulus to the person;
the muscle activity information of each of the plurality of skeletal muscles of the person is acquired for each of the stimuli when each of the stimuli is applied to the person, whereas the subjective evaluation information is acquired, in the step of acquiring the muscle activity information; and
the psychological state of the person when the each subjective evaluation information is acquired is specified based on the subjective evaluation information of the person to specify the psychological state of the person when the each muscle activity information corresponding to the each subjective evaluation information is acquired, thereby associating the each muscle activity information with the psychological state of the person, in the selecting step.

6. The method of selecting the specific skeletal muscle according to claim 1, wherein all the plurality of skeletal muscles of the person are muscles which are not active for an operation performed by the person.

7. The method of selecting the specific skeletal muscle according to claim 6, wherein the plurality of skeletal muscles of the person include at least one of a masticatory muscle and a mimetic muscle of a face of the person.

8. A method of evaluating a stress on a person during an operation, comprising:
a step of acquiring muscle activity information of a person during an operation for a specific skeletal muscle of the person selected by the method of claim 1; and
a step of evaluating a degree of stress placed on the person during the operation based on the acquired muscle activity information of the specific skeletal muscle.

9. The method of selecting the specific skeletal muscle according to claim 1, wherein the first stimulus is at least one of an algesic stimulus, an olfactory stimulus and an auditory stimulus, and the external stimulus applying means is at least one of a finger-pressure device for applying the algesic stimulus to the person, an aroma generator for applying the olfactory stimulus to the person, and a sound generator for applying the auditory stimulus to the person.

10. An apparatus for selecting a specific skeletal muscle affected by a psychological state of a person from a plurality of skeletal muscles of the person in order to evaluate a stress on the person during an operation, comprising:
means for acquiring muscle activity information of each of a plurality of different skeletal muscles of the person;
means for applying at least a first stimulus directly to at least one sense organ of the person with an external stimulus applying means to bring the person into an uncomfortable state, the first stimulus being different from a stimulus applied to the person during the operation in which the stress is evaluated; and
means for selecting the specific skeletal muscle based on the muscle activity information of each of the plurality of skeletal muscles of the person when the person is brought into the uncomfortable state by the first stimulus.

11. The apparatus for selecting the specific skeletal muscle according to claim 10, wherein the first stimulus is at least one of an algesic stimulus, an olfactory stimulus and an auditory stimulus, and the external stimulus applying means is at least one of a finger-pressure device for applying the algesic stimulus to the person, an aroma generator for applying the olfactory stimulus to the person, and a sound generator for applying the auditory stimulus to the person.

12. The apparatus for selecting the specific skeletal muscle according to claim 10, further comprising;
means for acquiring subjective evaluation information of the person indicating the psychological state of the person when the muscle activity information of each of the plurality of skeletal muscles of the person is acquired, for the each stimulus when the each stimulus is applied to the person,
wherein the psychological state of the person when the each subjective evaluation information is acquired is specified based on the subjective evaluation information of the person acquired by the means of acquiring the subjective evaluation information.

13. The apparatus for selecting the specific skeletal muscle according to claim 10, wherein the selecting means receives the muscle activity information of each of the plurality of different skeletal muscles of the person when the person is in a relaxing state to select a muscle having a larger amount of change in the muscle activity information when the person is brought into the uncomfortable state by the first stimulus with respect to the muscle activity information in the relaxing state as compared with a set first threshold value, as the specific skeletal muscle from the plurality of skeletal muscles of the person.

14. A system for evaluating a stress during an operation, comprising:
the apparatus for selecting the specific skeletal muscle according to claim 10;
means for acquiring the muscle activity information of the specific skeletal muscle of the person during the operation, the specific skeletal muscle of the person being selected by the selecting means of the apparatus for selecting the specific skeletal muscle; and means for evaluating a degree of the stress placed on the person during the operation based on the acquired muscle activity information of the specific skeletal muscle.

15. The system for evaluating the stress during the operation according to claim 14, further comprising:

means of acquiring subjective evaluation information of the person indicating the psychological state of the person when the muscle activity information of each of the plurality of skeletal muscles of the person is acquired, for the each stimulus when the each stimulus is applied to the person, wherein the psychological state of the person when the each subjective evaluation information is acquired is specified based on the subjective evaluation information of the person acquired by the means of acquiring the subjective evaluation information.

* * * * *